United States Patent [19]

Cooley et al.

[11] 3,963,028

[45] June 15, 1976

[54] SUCTION WAND

[75] Inventors: Denton A. Cooley; Charles C. Reed, both of Houston; Russell G. Sharp, Sugar Land, all of Tex.

[73] Assignee: Texas Medical Products, Inc., Houston, Tex.

[22] Filed: Feb. 6, 1975

[21] Appl. No.: 547,529

[52] U.S. Cl. .............................................. 128/276
[51] Int. Cl.² ........................................ A61M 1/00
[58] Field of Search ........................ 128/275–278, 128/239, 240; 32/33

[56] References Cited
UNITED STATES PATENTS

| 3,109,426 | 11/1963 | Noonan et al. | 128/276 |
| 3,256,885 | 6/1966 | Higgins et al. | 128/276 |
| 3,426,759 | 2/1969 | Smith | 128/276 |

FOREIGN PATENTS OR APPLICATIONS

| 1,491,755 | 10/1969 | Germany | 128/276 |

*Primary Examiner*—Robert W. Michell
*Assistant Examiner*—Henry S. Layton
*Attorney, Agent, or Firm*—H. Ross Workman; J. Winslow Young

[57] ABSTRACT

A suction wand having a weighted, reusable handle in cooperation with a disposable suction conduit, the suction conduit having a suction tip at one end and adapted to couple with a suction tubing at the other end. The weighted handle imparts a pre-selected weight and feel to the wand and is selectively reusable with a variety of disposable suction conduit systems.

2 Claims, 2 Drawing Figures

SUCTION WAND

BACKGROUND

1. Field of the Invention

This invention relates to suction wands useful in surgical procedures and methods for producing same.

2. The Prior Art

Suction devices are commonly used in a variety of medical applications to evacuate various fluids from a patient for a variety of purposes. For example, during surgery, blood and other body fluids are commonly removed to permit visual inspection of the surgical site and disposal of the fluids. Historically, suction wands (commonly referred to as "sucker tips") useful for these procedures have been fabricated from metal and were, accordingly, reusable only after suitable cleaning and sterilization. However, with the recent advent of disposable surgical equipment including suction wands, metal suction wands have been almost entirely replaced by the cheaper, light weight, disposable suction wand systems fabricated from plastics.

Although the disposable suction wand systems have provided a number of advantages particularly with respect to convenience, they have demonstrated a tendency to create additional problems relating to maintaining an aseptic condition within the surgical area. Being of light weight, and attached to an extended length of heavier, flexible suction tubing, it has been found that the weight of the suction tubing has a tendency to pull the wand off the sterile operating table into the non-sterile area below the table.

Furthermore, surgeons have discovered that they do not prefer the disposable suction device in spite of its many advantages primarily because the disposable devices do not have the weight or "heft" of the metallic suction devices. Accordingly, what is needed is a suction wand which advantageously incorporates the desirable features of a disposable suction wand and weight of a reusable suction wand. The device should preferably include as the disposable portion all those segments of the suction wand which come in contact with the fluids being aspirated. The wand should also include a weighted portion to impart the preferred feel to the device and also serve to hold the suction wand on the operating table.

Such an improved suction wand and process for manufacturing the same is provided by the present invention.

BRIEF SUMMARY AND OBJECTS OF THE INVENTION

The present invention provides a suction wand wherein the fluids suction conduit is fabricated from plastic so as to be readily disposable and is adapted to be telescopically received in a handle portion which has been fabricated from metal so as to impart the desired weight to the suction wand. The fluid conduit may be fabricated as a unitary piece or may preferably be fabricated as components which assemble into a fluid conduit. The metal handle includes an axial through-bore and preferably includes a tapered section so as to releasably engage the fluid suction conduit in a press fit relationship.

It is therefore a principal object of this invention to provide improvements in suction wands.

It is another object of this invention to provide a suction wand having a disposable portion and a nondisposable portion, the disposable portion, being the fluid conduit with the handle serving as the reusable portion.

Another object of this invention is to provide a suction wand wherein the handle has an axial through bore tapered so as to engage the fluid conduit in a releasable press fit relationship.

One further object of this invention is to provide an improved method for fabricating suction wands.

These and other objects and features of the present invention will become more fully apparent from the following description and appended claims taken in conjunction with the accompanying drawing.

DETAILED DESCRIPTION OF THE PREFERRED EMBODIMENTS

Figure 1:
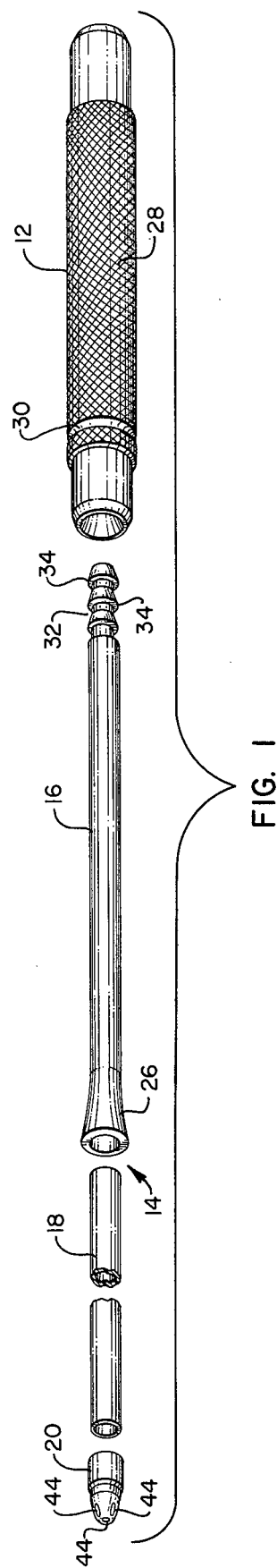
FIG. 1 is an exploded perspective view of one preferred embodiment of the invention.

The invention is best understood by reference to the drawing wherein like parts are designated with like numerals throughout.

The Structure

Figure 2:
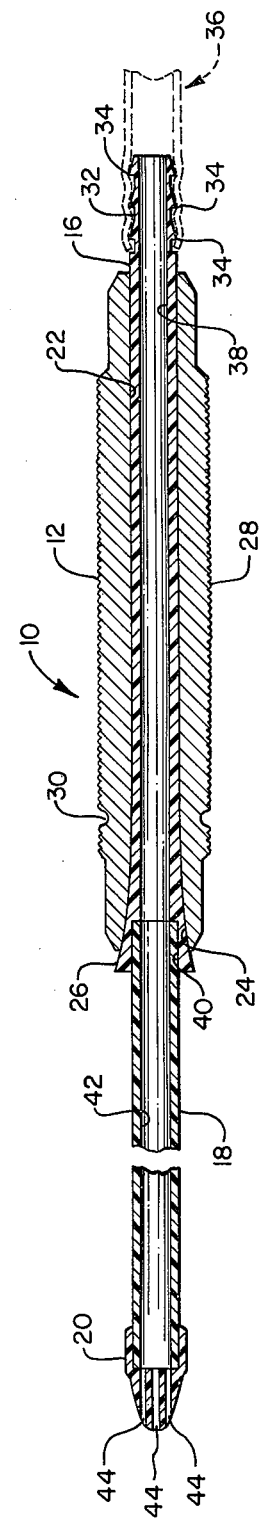
FIG. 2 is a cross-section of the assembled embodiment of FIG. 1.

In one presently preferred embodiment of the invention as illustrated in FIGS. 1 and 2, a suction wand is shown generally at 10 and includes a weighted handle 12 and a suction conduit 14 cooperating therewith. The suction conduit 14 includes an insert 16, a probe 18 and a suction tip 20, the function of each of which will be discussed more fully hereinafter.

Turning with particular attention to handle 12, handle 12 is preferably fabricated from a suitable metal such as stainless steel or the like. The metal imparts the desired weight characteristics to the suction wand 10 and is readily susceptible to sterilization prior to use. Handle 12 includes a through-bore 22 which is tapered (shown exaggerated for purposes of illustration) at least a portion of its distance as indicated at 24 so as to engage a corresponding flared portion 26 of insert 16 as will be discussed more fully hereinafter. Handle 12 includes a knurled section 28 and a groove 30 or other indicia to serve as an indicator of the forward or tapered end of the handle 12 to assist personnel in assembling the suction wand 10 of the present invention.

Turning now with particular reference to suction conduit 14, the insert 16 includes a flare 26 (shown exaggerated for purposes of illustration) at one end and a tubing coupling 32 at the other end. Flare 26 cooperates in press fit relationship with taper 24 (also shown correspondingly exaggerated for purposes of illustration) so as to releasably retain insert 16 in through bore 22 of handle 12.

Tubing coupling 32 includes a plurality of annular collars 34 which engage the internal diameter of a suction tubing 36 as shown in broken lines (FIG. 2). Insert 16 includes a through-bore 38 so as to provide fluid communication through handle 12. The forward end of through-bore 38 is provided with a counter-bore 40 which is configured so as to receive one end of probe 18 in a press fit relationship. Probe 18 has an axial through-bore 42 which, when probe 18 is connected to insert 16, provides continuity with through-bore 38 of insert 16.

Probe 18 is shown herein as broken and foreshortened for sake of simplicity, however, clearly probe 18 may be of any suitable configuration including angular and of any suitable length and dimension. The probe 18, in combination of the suction tip 20, may be selectively assembled with insert 16 so as to provide the surgical personnel with a suction wand to meet any of a number of selected conditions. For example, the suction wand may be used for a variety of purposes including a suction wand for adult cardiac, pediatric cardiac, tip suction, graft suction, and general purpose wand including a square tip or an angle tip and a heart valve holder. The particular configuration of suction wands for each of these purposes is well known in the art and their presentation herein is deemed unnecessary as this tip configuration is incidential to this invention.

Suction tip 20 in this illustrated embodiment is configurated so as to engage probe 18 in a press fit relationship with apertures 44 in direct fluid communication with through-bore 42 of probe 18. Apertures 44 act as a screen to prevent the aspiration of tissue matter which would otherwise obstruct and clog the wand 10 and/or suction conduit 14.

The Process

As illustrated in the presently preferred embodiment of this invention, suction conduit 14 is indicated as being fabricated from three discrete parts, that is, insert 16, probe 18, and suction tip 20. However, suction conduit 14 may be fabricated as a unitary suction conduit terminating at one end in a perforated suction tip similar to suction tip 20 and at the other end in a tubing coupling similar to tubing coupling 32. The suction conduit, if fabricated as a unitary piece, should also include a flared portion similar to flare 26 of insert 16 so as to engage the taper 24 of handle 12 in a press fit relationship thereby releasably locking the suction conduit in the through-bore 22 of handle 12.

It is preferable, however, for the purposes of this invention that each of the tip 20, probe 18 and insert 16 be separately fabricated and thereafter bonded together as a unitary conduit 14. Although each of the insert 16, probe 18, and tip 20 are preferably unitarily bonded together into a conduit 14, their separate manufacture greatly facilitates the fabrication of an increased plurality of conduits 14 from a relatively few injection mold forms for insert 16, probe 18, and tip 20. The number of possible combinations for conduit 14 are far greater than the number of mold forms required for the fabrication of the separate interchangeable components that combine to form the conduit 14.

Once the selected components (insert, probe, and tip) are selected for a particular configuration for a conduit 14, the components are bonded together into a unitary conduit 14. In this manner, a suction tip 20 having one of a variety of dimensions and configurations can be fitted to a probe 18 having one of a variety of dimensions and configurations. Subsequently, attachment of the tip 20 and probe 18 combination to an insert 16 provides a custom-fabricated conduit 14 for a wand 10 which is now adapted for a highly specific use as determined by the selection of the tip 20 and probe 18.

This process for fabricating conduit 14 advantageously provides a greater number of possible conduit combinations over the relatively few mold forms for tip and probe assemblies.

Clearly, either embodiment would be suitable within the context of the present invention since the present invention is directed toward the concept of providing a suction wand with a disposable fluids handling system and a reusable weighted handle. Accordingly, what is provided herein is a unique combination of disposable and reusable parts, the reusable part being fabricated from a metal such as stainless steel to impart the preferred weight and feel to the suction wand while simultaneously providing an inexpensive, disposable fluids handling conduit which cooperates with the weighted handle.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A surgical suction wand comprising:
    a weighted handle of metal construction, the handle comprising a single axial, generally cylindrical through-bore opening at the leading end and at the trailing end of the handle, the leading end of the through-bore tapering outwardly;
    an elongated suction conduit comprising a unitary, generally cylindrical insert having an external configuration which corresponds to the through-bore within the handle, the insert tapering outwardly at its leading end;
    the external surface of the insert defining a diameter which is essentially the same as the diameter of the through-bore, said insert being telescopically surmounted by the handle and releasably attached thereto with a press-fit coupling, the through-bore receiving the insert in snug relationship along the entire length of the bore; and
    a coupling for flexible suction tubing integral and coextensive with the trailing end of the insert, said coupling projecting beyond the trailing end of the handle when the handle surmounts the insert.

2. A surgical suction wand as defined in claim 1 wherein said handle comprises indicia for identifying the leading end thereof.

* * * * *